United States Patent
Metz et al.

(10) Patent No.: US 8,133,997 B2
(45) Date of Patent: Mar. 13, 2012

(54) 2,4-DIOXOPYRIMIDINE-BASED MESOIONIC PIGMENTS

(75) Inventors: Thomas Metz, Heppenheim (DE); Carsten Plueg, Seeheim-Jugenheim/Ober-Beerbach (DE)

(73) Assignee: Clariant Produkte (Deutschland) GmbH, Frankfurt (DE)

( * ) Notice: Subject to any disclaimer, the term of this patent is extended or adjusted under 35 U.S.C. 154(b) by 1600 days.

(21) Appl. No.: 10/587,694

(22) PCT Filed: Jan. 14, 2005

(86) PCT No.: PCT/EP2005/000305
§ 371 (c)(1), (2), (4) Date: Jul. 27, 2006

(87) PCT Pub. No.: WO2005/070928
PCT Pub. Date: Aug. 4, 2005

(65) Prior Publication Data
US 2007/0185325 A1    Aug. 9, 2007

(30) Foreign Application Priority Data
Jan. 27, 2004   (DE) .......................... 10 2004 003 888

(51) Int. Cl.
*C07D 491/00* (2006.01)
*C07D 495/00* (2006.01)

(52) U.S. Cl. ...................................... 544/278
(58) Field of Classification Search .................. 544/278; 514/259.1
See application file for complete search history.

(56) References Cited

U.S. PATENT DOCUMENTS

| | | | |
|---|---|---|---|
| 4,525,591 A | 6/1985 | Lotsch et al. | |
| 5,663,309 A * | 9/1997 | Hurter | 534/763 |
| 6,872,245 B2 | 3/2005 | Grimm et al. | |

OTHER PUBLICATIONS

Friedrichsen et al., Heterocycles 1982, 19, pp. 1083-1148.*
Matyjas et al., AUTEX Research, vol. 3, No. 2 (2003).*
PCT International Search Report for PCT/EP2005/000305, mailed May 20, 2005.
English Translation of the PCT International Preliminary Report on Patentability, mailed Oct. 12, 2006.
Friedrichsen et al., "Six-membered Mesoionic Heterocycles of the m-Quinodimethane Dianion Type," pp. 1083-1148, Heterocycles, vol. 19, No. 6; 1982.
Plug et al., "Mesionic pyridopyrimidinylium and pyridooxazinylium olates and Non-Mesoionic Pyridopyrimidinones. Structures in Solid State, Solutions and Matrices," J. Chem. Soc. Perkin Trans. 2, pp. 2096-2108; 2000.
Hisano et al., "Reaction of Aromatic", N-Oxides with Dipolarophiles. IV Factors Affecting the 1,3-Cycloaddition of Pyridine 1-Oxide with Phenyl Isocyanates, Chem. Phar. Bull. vol. 29, pp. 3706-3712; 1981.
Laackmann et al., "Bis-(Pyrimidinium olates)," Tetrahedron, vol. 52, No. 15, pp. 5475- 5486; 1996.

* cited by examiner

*Primary Examiner* — Paul V. Ward
(74) *Attorney, Agent, or Firm* — Anthony A. Bisulca

(57) ABSTRACT

The invention relates to the dimeric compound of formula (II)

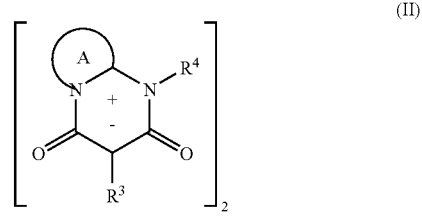

wherein the two monomer-units are linked with each other either via $R^3$ or via $R^4$; the ring A is a five-or six-membered heteroaromatic ring, one of the groups $R^3$ or $R^4$ is an unsubstituted or substituted phenylene radical, the remaining group $R^3$ or $R^4$ is a $C_1$-$C_4$ alkyl, $C_5$-$C_6$ cycloalkyl, an unsubstituted or substituted phenyl, benzyl, benzanilide or naphthyl; or wherein the group $NR^4$ together with the ring A constitutes a five-or six membered heterocycle that can be annelated with a benzene ring, and $R^3$ is an unsubstituted or substituted phenylene radical. The inventive compounds can be used for pigmenting high-molecular organic materials.

10 Claims, No Drawings

2,4-DIOXOPYRIMIDINE-BASED MESOIONIC PIGMENTS

The present invention relates to novel, mesoionic compounds, to a process for their preparation and to their use as pigments.

The literature [W. Friedrichsen, T. Kappe, A. Böttcher, Heterocycles 1982, 19, 1083-1148; C. Wentrup et al., J. Chem. Soc, Perkin Trans 2 2000, 2096-2108] describes mesoionic compounds of formula (I)

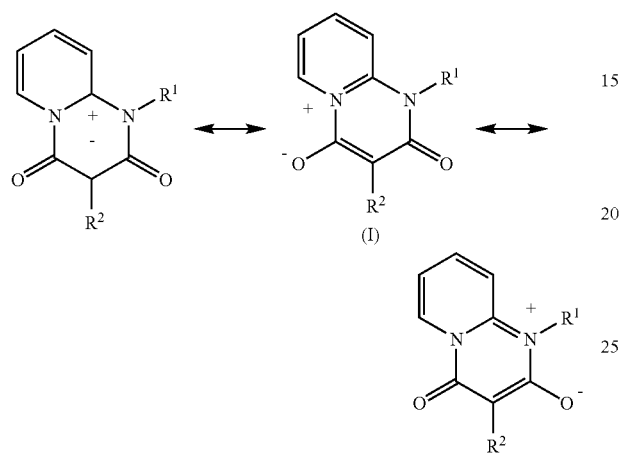

where $R^1$ is methyl or phenyl and $R^2$ is methyl or hydrogen. In what follows, only the notation shown first will be used for mesoions. These compounds have high melting points and are described as yellow crystals. In the course of their preparation, it was observed that they exhibit solid state fluorescence, but are not useful as pigments because of their low color strength.

Solid state fluorescent pigments are remarkably rare. Commercially available colorants such as Pigment Yellow 101 and the so-called fluorescent pigments, which are based on incorporation of dyes in polymers, do not satisfy the need since the stability of these pigments to light is insufficient for many fields of application.

It is an object of the present invention to provide luminescently colored and preferably fluorescent pigments that combine the high fastness properties of pigments, such as thermal stability, lightfastness, solvent fastness and also migration stability, with the brilliance of fluorescent dyes.

We have found that, surprisingly, a dimerization of compounds of formula (I) via a phenylene bridge distinctly enhances the color strength and also provides materials of pigmentary character.

The present invention accordingly provides dimeric compounds of formula (II)

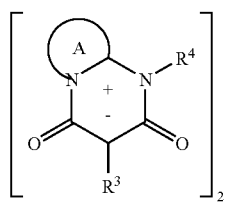

where the two monomeric units are linked either via $R^3$ or via $R^4$;

the ring A is a five- or six-membered heteroaromatic ring of structure A1 to A7

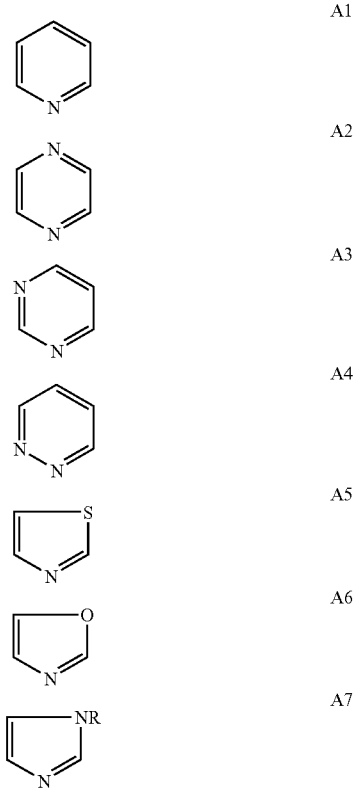

where the rings A1 to A7 are unsubstituted, $C_1$-$C_4$-alkyl or phenyl substituted and/or fused with a benzene ring, one of $R^3$ and $R^4$ is an unsubstituted or alkyl-, alkoxy- and/or halogen-substituted phenylene radical, the other one of $R^3$ and $R^4$ is $C_1$-$C_4$-alkyl, $C_5$-$C_6$- cycloalkyl, an unsubstituted or alkyl-, alkoxy-, nitro-, phenyl-, alkoxycarbonyl-, dialkylamino-, dialkylaminocarbonyl-, alkylaminocarbonyl-, aminocarbonyl- and/or halogen-substituted phenyl, benzyl, benzanilide, $C_5$-$C_6$-cycloalkyl or naphthyl; or where the $NR^4$ group may combine with the A ring to form a 5- or 6-membered heterocycle which may be additionally fused with a benzene ring, and $R^3$ is an unsubstituted or alkyl-, alkoxy- and/or halogen-substituted phenylene radical; and R is $C_1$-$C_4$-alkyl or phenyl.

Preferred compounds for the purposes of the present invention are compounds of the general formulae (IIa) and (IIb)

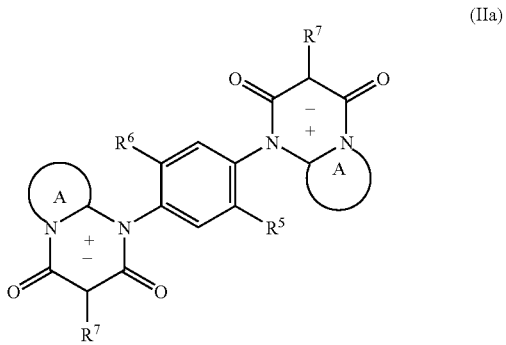

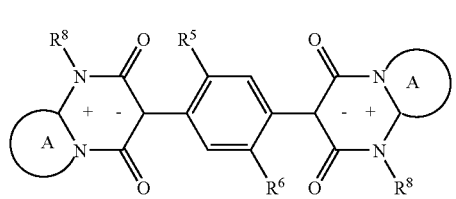

(IIb)

where A is as defined above, $R^5$ and $R^6$ are independently hydrogen, $C_1$-$C_4$-alkyl, $C_1$-$C_4$-alkoxy or halogen, preferably hydrogen, methyl or chlorine;

$R^7$ and $R^8$ are $C_1$-$C_4$-alkyl, $C_5$-$C_6$-cycloalkyl, a phenyl, benzyl, benzanilide or naphthyl that is unsubstituted or substituted by 1, 2, 3 or 4 radicals selected from the group consisting of $C_1$-$C_4$-alkyl, $C_1$-$C_4$-alkoxy, nitro, phenyl, $C_1$-$C_4$-alkoxycarbonyl, di($C_1$-$C_3$-alkyl)amino, di($C_1$-$C_3$-alkyl)aminocarbonyl, ($C_1$-$C_3$-alkyl)-aminocarbonyl, aminocarbonyl and/or chlorine;

or where the $NR^8$ group combines with the A ring to form a 5- or 6-membered heterocycle which may be additionally fused with a benzene ring, examples being pyrrole or a benzopyrrole.

The phenyl radical previously mentioned in the definition of $R^3$, $R^4$, $R^7$ and $R^8$ is preferably selected from the group consisting of 1-, 2-, 3-methyl-, ethyl-, methoxy-, ethoxy-, diethylamino-, chlorophenyl, 2,5-dichloro-, 3-chloro-4-methyl-, 3-chloro-4-methoxy- and 4-nitrophenyl.

Particular preference is given to compounds of formula (V)

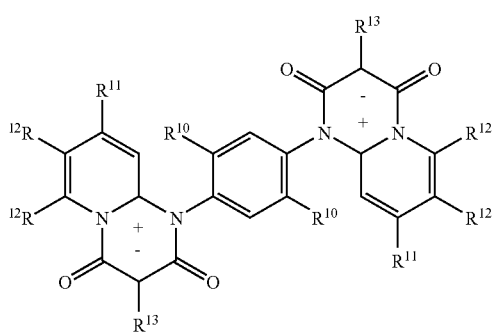

(V)

where $R^{10}$ is hydrogen, methyl or chlorine, $R^{11}$ is hydrogen or methyl, $R^{12}$ is hydrogen, or two adjacent $R^{12}$ radicals together are a divalent $C_4H_4$ radical, and $R^{13}$ is methyl or phenyl.

A broad color spectrum opens up for the pigments that gives access to yellow, red and green pigments, depending on the way the mesoionic compounds according to formula (IIa) or (IIb) are linked.

The present invention's compounds of formula (II) can be prepared from N-substituted rings of type A with amidine structure (III) and substituted malonyl chlorides (IV) according to the following scheme:

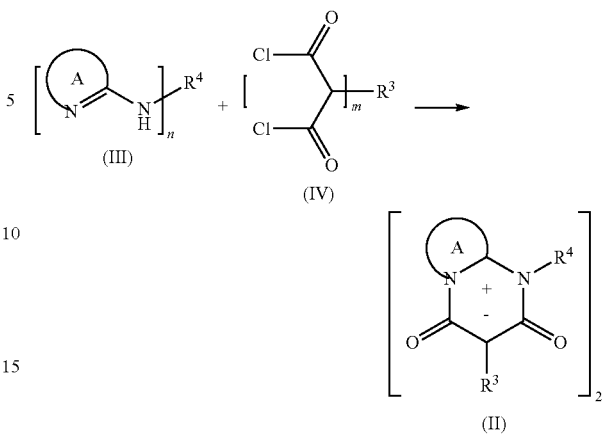

where either m=2 and n=1 or m=1 and n=2.

The present invention also provides a process for preparing compounds of formula (II), which comprises condensing either (a) one equivalent of the compound of formula (III) where n is 2 with about two equivalents of the compound of formula (IV) where m is 1; or (b) one equivalent of the compound of formula (IV) where m is 2 with about two equivalents of the compound of formula (III) where n is 1.

In case (a), the reaction mixture advantageously utilizes 2 to 5 mol equivalents and preferably 3.5 to 4 mol equivalents of compound (IV) per one mol equivalent of compound (III).

In case (b), the reaction mixture advantageously utilizes 2 to 3 mol equivalents and preferably 2 to 2.5 mol equivalents of compound (III) per one mol equivalent of compound (IV).

The compounds of formulae (III) and (IV) are literature known or obtainable similarly to known processes [T. Hisano, T. Matsuoka, K. Tsutsumi, K. Muraoka, M. Ichikawa, Chem. Pharm. Bull., 1981, 29 (12), 3706-3712; P. Laackmann, W. Friedrichsen, Tetrahedron, 1996, 52, 5475-5486.].

It will be particularly advantageous to conduct the condensation in the presence of a base, preferably of 1 to 5 equivalents and especially 2 to 5 equivalents of a base, based on the amidine (III). Useful bases include for example triethylamine, pyridine, picoline, N-methylimidazole or alkali metal carbonate.

However, it is also possible to conduct the condensation in the absence of a base, in which case, however, the yield of compound (II) may be reduced by incomplete condensation.

The condensation is advantageously carried out in an aprotic solvent, preferably methylene chloride, chloroform, N-methylpyrrolidone, dimethylformamide, o-dichlorobenzene, chlorobenzene, ethyl acetate, butyl acetate, acetone, methyl ethyl ketone, methyl i-butyl ketone, methyl t-butyl ether, tetrahydrofuran, dioxane or propylene glycol dimethyl ether, at temperatures from −10 to +100° C. and preferably 50 to 80° C.

The compounds of the present invention are filtered off, washed free of by-produced reaction products, freed of the salts by stirring up with water and filtering, and if appropriate dried.

To improve their pigmentary properties, the compounds of the present invention may be additionally subjected to a fine-dividing operation, for example a grinding operation, and/or a thermal treatment in an aqueous, aqueous-organic or organic medium at temperatures between 40° C. and 200° C., if appropriate under superatmospheric pressure. Subsequently, the pigment suspensions obtained can be conventionally filtered, the press cake washed salt free with water, dried and ground.

The compounds of the present invention are useful for pigmentation of macromolecular organic materials of natural or synthetic origin, for example of plastics, resins, coatings, paints, electrophotographic toners and developers, electret materials, color filters and also of inks, including printing inks, and seed.

Macromolecular organic materials which can be pigmented with the compounds of the present invention are for example cellulose compounds, for example cellulose ethers and esters, such as ethylcellulose, nitrocellulose, cellulose acetates or cellulose butyrates, natural binders, for example fatty acids, fatty oils, resins and their conversion products, or manufactured resins, such as polycondensates, polyadducts, addition polymers and addition copolymers, such as for example amino resins, especially urea- and melamine-formaldehyde resins, alkyd resins, acrylic resins, phenoplasts and phenolic resins, such as novolaks or resoles, urea resins, polyvinyls, such as polyvinyl alcohols, polyvinyl acetals, polyvinyl acetates or polyvinyl ethers, polycarbonates, polyolefins, such as polystyrene, polyvinyl chloride, polyethylene or polypropylene, poly(meth)acrylates and their copolymers, such as polyacrylic esters or polyacrylonitriles, polyamides, polyesters, polyurethanes, coumarone-indene and hydrocarbon resins, epoxy resins, unsaturated manufactured resins (polyesters, acrylates) having various curing mechanisms, waxes, aldehydic and ketonic resins, gum, rubber and its derivatives and latices, casein, silicones and silicone resins; individually or in admixtures. It is immaterial whether the macromolecular organic compounds mentioned are in the form of plastically deformable compositions, melts or in the form of spinning solutions, dispersions, coatings, paints or nonjettable printing inks. Depending on the intended use, it will be advantageous to use the compounds of the present invention as a blend or in the form of formulations or dispersions. Based on the macromolecular organic material to be pigmented, the compounds of the present invention are used in an amount of from 0.05% to 30% by weight and preferably 0.1% to 15% by weight.

It is also possible in some cases to use a crude having a BET surface area of greater than 2 $m^2$/g and preferably greater than 5 $m^2$/g instead of a corresponding ground and/or finished compound of the present invention. This crude can be used for producing color concentrates in liquid or solid form in concentrations from 5% to 99% by weight, alone or if appropriate in admixture with other crudes or ready-produced pigments.

The compounds of the present invention are also useful as a colorant in electrophotographic toners and developers, for example one- or two-component powder toners (also known as one- or two-component developers), magnetic toners, liquid toners, latex toners, addition polymerization toners and also specialty toners.

Typical toner binders are addition polymerization, polyaddition and polycondensation resins, such as styrene, styrene-acrylate, styrene-butadiene, acrylate, polyester and phenol-epoxy resins, polysulfones, polyurethanes, individually or in combination, and also polyethylene and polypropylene, which may each contain further ingredients, such as charge control agents, waxes or flow assistants, or may subsequently be modified with these additives.

The compounds of the present invention are further useful as a colorant in powders and powder coatings, especially in triboelectrically or electrokinetically sprayable powder coatings used for surface coating of articles composed for example of metal, wood, plastic, glass, ceramic, concrete, textile material, paper or rubber.

Useful powder coating resins typically include epoxy resins, carboxyl- and hydroxyl-containing polyester resins, polyurethane and acrylic resins together with customary hardeners. Combinations of resins can also be used. For instance, epoxy resins are frequently used in combination with carboxyl- and hydroxyl-containing polyester resins. Typical hardener components (depending on the resin system) include for example acid anhydrides, imidazoles and also dicyandiamide and descendents thereof, blocked isocyanates, bisacylurethanes, phenolic and melamine resins, triglycidyl isocyanurates, oxazolines and dicarboxylic acids.

The present invention further provides for the use of the colorant preparations described as a colorant for jettable printing inks, especially for inkjet inks. Inkjet inks refers not only to inks on an aqueous basis (including microemulsion inks) and on a nonaqueous basis (solvent-based), UV-curable inks but also to such inks as operate by the hot melt process.

Solvent-based inkjet inks contain essentially 0.5% to 30% by weight and preferably 1% to 15% by weight of the compounds of the present invention, 70% to 95% by weight of an organic solvent or solvent mixture and/or of a hydrotropic compound. If appropriate, the solvent-based inkjet inks can contain carrier materials and binders which are soluble in the solvent, examples being polyolefins, natural rubber, synthetic rubber, polyvinyl chloride, vinyl chloride-vinyl acetate copolymers, poly(vinyl butyral)s, wax-latex systems or combinations thereof.

If appropriate, solvent-based inkjet inks may include further additives, examples being wetting agents, degassers/defoamers, preservatives and antioxidants. Microemulsion inks are based on organic solvents, water and if appropriate an additional substance (surfactant) which acts as an interfacial mediator. Microemulsion inks contain 0.5% to 30% by weight and preferably 1% to 15% by weight of the compounds of the present invention, 0.5% to 95% by weight of water and 0.5% to 95% by weight of organic solvents and/or interfacial mediators.

UV-curable inks contain essentially 0.5% to 30% by weight of the compounds of the present invention, 0.5% to 95% by weight of water, 0.5% to 95% by weight of an organic solvent or solvent mixture, 0.5% to 50% by weight of a radiation-curable binder and if appropriate 0% to 10% by weight of a photoinitiator.

Hot melt inks are usually based on waxes, fatty acids, fatty alcohols or sulfonamides which are solid at room temperature and liquefy on heating, the preferred melting range being between about 60 and about 140° C. Hot melt inkjet inks consist essentially of 20% to 90% by weight of wax and 1% to 10% by weight of the compounds of the present invention. They may further include 0% to 20% by weight of an additional polymer (as "dye dissolver"), 0% to 5% by weight of dispersant, 0% to 20% by weight of viscosity modifier, 0% to 20% by weight of plasticizer, 0% to 10% by weight of tackifying additive, 0% to 10% by weight of transparency stabilizer (prevents crystallization of waxes, for example) and also 0% to 2% by weight of an antioxidant.

The present invention's jettable printing inks, especially inkjet inks, can be produced by dispersing the present invention's compounds into the microemulsion medium, into the nonaqueous medium or into the medium for producing the UV-curable ink or into the wax for producing a hot melt inkjet ink. Advantageously, the as-obtained printing inks for inkjet applications are subsequently filtered, for example through a 1 μm filter.

The compounds of the present invention are further useful as a colorant for color filters, not only for additive but also for subtractive color generation, and also as a colorant for electronic inks ("e-inks") or electronic paper ("e-paper"). To produce color filters, not only reflecting but also transparent color filters, pigments are applied in the form of a paste or as a pigmented photoresist in a suitable binder (acrylates, acrylic esters, polyimides, polyvinyl alcohols, epoxides, polyesters, melamines, gelatin, caseins) to the respective LCD components (e.g. TFT-LCD=Thin Film Transistor Liquid Crystal Displays or for example ((S) TN-LCD=(Super) Twisted Nematic-LCD). As well as a high thermal stability, a high pigment purity is a prerequisite for a stable paste or a pigmented photoresist. In addition, the pigmented color filters can also be applied by inkjet printing processes or other suitable printing processes.

To evaluate the coating properties of the pigments produced according to the invention an aromatic alkyd-melamine resin varnish (AM varnish) based on a medium-oil non-drying alkyd resin was selected from the multiplicity of existing coatings.

The pigments of the present invention are notable for good fastness properties; more particularly, they simultaneously possess high color strengths and high solvent fastnesses or high lightfastnesses. They are free of the environmentally unsafe heavy metals. The recited properties make the pigments of the present invention particularly useful as colorants in the printing sector (especially nonjettable printing inks, production of inkjet inks) and also for use in coatings and in plastics, color filters and toners.

Equivalents refers to mole equivalents in the examples which follow.

EXAMPLES

A) Preparation of 1,4-phenylenedimalonic acid:
To a cooled suspension, at 0 to 5° C., of 78.9 g (0.20 mol) of tetraethyl 1,4-phenylenedimalonate in 800 ml of ice-water are added 56.8 g (0.86 mol) of KOH (powder, 85% pure) dissolved in 800 ml of water dropwise over 20 min. This is followed by refluxing for 2.5 h, during which about 180 ml of the solvent are distilled out of the reaction mixture. After cooling, the reaction mixture is cooled in an ice bath and admixed dropwise with 1000 ml of 2N HCl (pH 1) and subsequently extracted with 8×500 ml of ethyl acetate. The combined ethyl acetate extracts are dried over $Na_2SO_4$ and concentrated to dryness under reduced pressure. Recrystallization from tetrahydrofuran/cyclohexane yields 41.2 g (73%) of colorless crystals of melting point 251-254° C. The product obtained is used for preparing 1,4-phenylenedimalonyl chloride.

B) General Prescription for Preparing the malonyl chloride Derivatives from methylmalonic acid, phenylmalonic acid and 1,4-phenylenedimalonic acid:
To a solution of 1 equivalent of the corresponding malonic acid derivative in dichloromethane are added 4.5 equivalents of phosphorus pentachloride and stirred at about 20° C. for 2 h. Dissolved HCl gas is removed under reduced pressure (about 200 mbar, 45 min). The entire reaction mixture is then concentrated to dryness at about 40° C. under reduced pressure. The malonyl chloride obtained is directly used in the synthesis of mesoionic compounds ("variant A-D").

C) General Prescription for Preparing mesoionic pigments
The respective reaction conditions are summarized in Table 1 and Table 2.

Variant A
To 2.5 equivalents of malonyl chloride derivative (preparation see General Prescription), dissolved in the solvent used, is gradually added at room temperature a solution of 1 equivalent of amidine in the solvent used, over 1.5-3.0 h. On completion of the addition the reaction mixture is stirred at room temperature for 18-20 h. After cooling, the product is filtered and washed with the solvent used and dried (80-100° C.).

Variant B
To 4 equivalents of malonyl chloride derivative (preparation see General Prescription), dissolved in the solvent used, is gradually added at 50-60° C. a solution/suspension of 1 equivalent of amidine and 4.5 equivalents of triethylamine in the solvent used, over 0.5-3.0 h. On completion of the addition the reaction mixture is stirred under reflux for 18-20 h. After cooling, the product is filtered and washed with the solvent used. The filter press cake obtained is suspended in water, filtered, washed salt free with water and dried (80-100° C.).

Variant C
To 4.0 equivalents of malonyl chloride derivative (preparation see General Prescription), dissolved in the solvent used, is added 1 equivalent of amidine at 20° C. with vigorous stirring. A mixture of 4.5 equivalents of triethylamine in the solvent used is then gradually added over 0.5-3.0 h. On completion of the addition the reaction mixture is stirred under reflux for 18-20 h. After cooling, the product is filtered and washed with the solvent used. The filter press cake obtained is suspended in water, filtered, washed salt free with water and dried (80-100° C.).

Variant D
Under reflux, a solution of 2.2 equivalents of amidine and 4.5 equivalents of triethylamine in the stated solvent is admixed dropwise over 0.5-2.5 h with a solution of 1 equivalent of 1,4-phenylenedimalonyl chloride (preparation see General Prescription) in the stated solvent. The reaction mixture is stirred under reflux for 18-20 h. After cooling, the product is filtered off and washed with the solvent used. The filter press cake obtained is suspended in water, filtered and washed salt free with water and dried (80-100° C.).

D) Aftertreatment of Pigments
The as-obtained crude pigment ("variant A-D") is aftertreated by stirring under reflux in the solvent used, filtering, washing, drying (80-100° C.) and grinding.

Examples 1 to 14

Examples 1 and 2 are comparative examples.

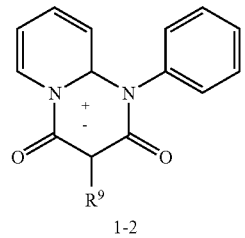

1-2

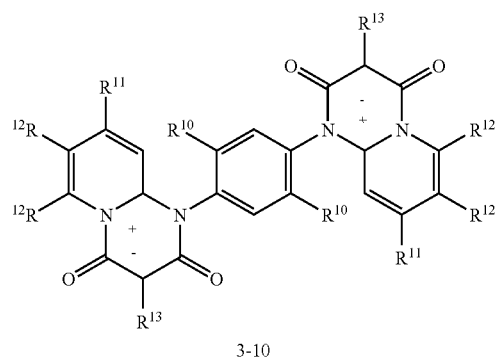

3-10

| Example | $R^9$ | $R^{10}$ | $R^{11}$ | $R^{12}$ | $R^{13}$ |
|---|---|---|---|---|---|
| 1 | Me | — | — | — | — |
| 2 | Ph | — | — | — | — |
| 3 | — | H | H | H | Me |
| 4 | — | H | H | H | Ph |
| 5 | — | Me | H | H | Me |
| 6 | — | Me | H | H | Ph |
| 7 | — | Cl | H | H | Me |
| 8 | — | Cl | H | H | Ph |
| 9 | — | H | Me | H | Ph |
| 10 | — | H | H |  | Ph |

TABLE 1
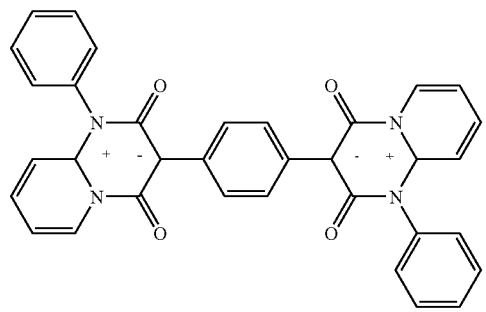
11
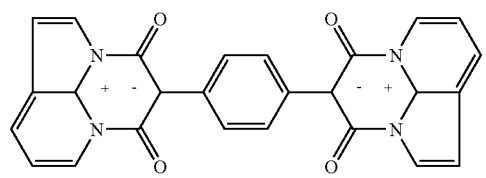
12
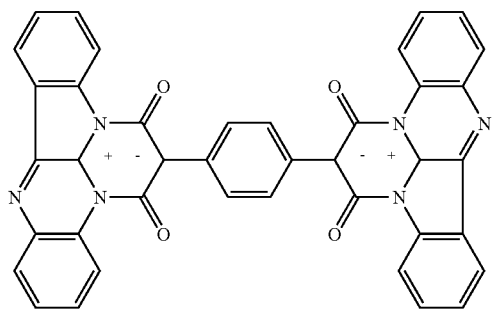
13
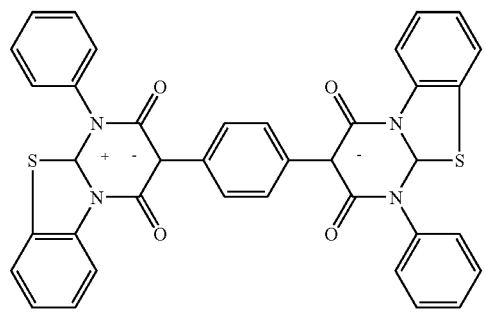
14
Reaction conditions/aftertreatment/yields
| Ex. | Variant | Malonyl chloride | Batch size [mol] [1] | Solvent (Malonyl chloride/ amidine) | After-treatment [2] | Yield [%] |
| --- | --- | --- | --- | --- | --- | --- |
| 1 | A | methyl- | 0.2 | CH$_2$Cl$_2$ (300/250 ml) | — | 53 |
| 2 | A | phenyl- | 0.2 | CH$_2$Cl$_2$ (300/150 ml) | — | 34 |
| 3 | B | methyl- | 0.125 | MEK (400/1850 ml) | DMF/MeOH | 71 |
| 4 | B | phenyl- | 0.1 | MEK (300/1500 ml) | CHCl$_3$ | 89 |
| 5 | C | methyl- | 0.1 | MEK (500/200 ml) | DMF/CHCl$_3$ | 32 |
| 6 | C | phenyl- | 0.1 | MEK (500/200 ml) | DMF | 89 |
| 7 | B | methyl- | 0.074 | CHCl$_3$ (250/1000 ml) | DMF/i-BuOH | 38 |
| 8 | B | phenyl- | 0.1 | CHCl$_3$ (250/1500 ml) | DMF | 66 |

TABLE 1-continued

| | | | | | | |
|---|---|---|---|---|---|---|
| 9 | B | phenyl- | 0.08 | CHCl₃ (240/1500 ml) | DMF | 55 |
| 10 | C | phenyl- | 0.095 | CHCl₃ (500/200 ml) | DMF | 87 |
| 11 | D | 1,4-phenylenedi- | 0.022 | CH₂Cl₂ (50/75 ml) | DMF | 64 |
| 12 | D | 1,4-phenylenedi- | 0.022 | CH₂Cl₂ (50/75 ml) | — | 78 |
| 13 | D | 1,4-phenylenedi- | 0.022 | THF (50/75 ml) | — | 89 |
| 14 | D | 1,4-phenylenedi- | 0.022 | CH₂Cl₂ (50/75 ml) | DMSO | 27 |

[1] based on the amidine;
[2] under reflux 30-60 min.
DMF = dimethylformamide, DMSO = dimethyl sulfoxide, MEK = methyl ethyl ketone, MeOH = methanol, THF = tetrahydrofuran.

TABLE 2

Physical data/pigment properties

| Ex. | Pigment color | Solid state fluorescence [3] | m.p. [° C.] | MALDI-TOF-MS (DHB, m/z, pos. mode) |
|---|---|---|---|---|
| 1 | greenish yellow | yes | 275-280 | 253.2 [M + H], 225.2 [M + H − CO] |
| 2 | greenish yellow | yes | 237-241 | 314.4 [M], 286.4 [M − CO] |
| 3 | greenish yellow | yes | 374-379 | 427.4 [M], 399.4 [M − CO] |
| 4 | yellow | yes | 352-357 | 551.6 [M], 522.6 [M − CO] |
| 5 | yellow | yes | 377-381 | 455.6 [M + H] |
| 6 | yellow | yes | 368-375 | 479.8 [M + H], 550.8 [M − CO] |
| 7 | yellow | yes | 377-381 | 493.1, 495.2, 497.1 [M − H], 461.2, 459.2 [M − HCl] |
| 8 | yellow | yes | 389-393 | 618.1, 620.1, 622.1 [M], 619.1, 621.1, 623.1, [M + H], 590.1, 592.1 [M − CO] |
| 9 | yellow | yes | 386-391 | 579.2 [M + H], 550.2 [M − CO] |
| 10 | orange | yes | 312-315 | 651.8 [M + H], 622.7 [M − CO] |
| 11 | reddish yellow | yes | 372-375 | 550.3 [M], 522.3 [M − CO] |
| 12 | red | no | >400 | 446.3 [M] |
| 13 | dark green | no | >400 | 648.8 [M], 621.8 [M + H − CO] |
| 14 | yellow | no | 359-364 | 662.5 [M], 634.5 [M − CO] |

[3] in UV light at 366 nm.
DHB = 2,5-dihydroxybenzoic acid
MALDI-TOF-MS = Matrix Assisted Laser Desorption Ionization − Time of Flight − Mass Spectrometry.

Use examples:

Table 3 indicates the solvent fastnesses and color strengths of the mesoionic comparative compounds 1 and 2 in comparison with the properties of the inventive compounds 4 and 11 obtained by dimerization.

TABLE 3

| Ex. | Pigment color | Solvent fastness | Color strength |
|---|---|---|---|
| 1 | greenish yellow | 3 | 0.10 |
| 2 | greenish yellow | 2 | 0.06 |
| 4 | yellow | 3-4 | 2.40 |
| 11 | reddish yellow | 4-5 | 1.58 |

Solvent fastness was determined in accordance with DIN 54002 against the 5-point gray scale.

Color strength indicates how many parts of $TiO_2$ are needed to reduce 1 part of chromatic pigment to ⅓ standard depth of shade: 1:×$TiO_2$ (color strength and its measurement is defined according to DIN EN ISO 787-26).

What is claimed is:

1. A compound of formula (II)

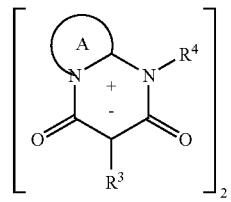

(II)

where the two monomeric units are linked either via $R^3$ or via $R^4$;
the ring A is a six-membered heteroaromatic ring of structure A1

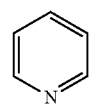

A1 where the ring A1 is unsubstituted, $C_1$-$C_4$-alkyl or phenyl substituted fused with a benzene ring or a combination thereof, one of $R^3$ and $R^4$ is an unsubstituted phenylene radical or a phenylene radical substituted by one or more of alkyl-, alkoxy- or halogen-substitutions, the other one of $R^3$ and $R^4$ is $C_1$-$C_4$-alkyl, $C_5$-$C_6$cycloalkyl, an unsubstituted phenyl, a phenyl substituted by one or more of alkyl-, alkoxy-, nitro-, phenyl-, alkoxycarbonyl-, dialkylamino-, dialkylaminocarbonyl-, alkylaminocarbonyl-, aminocarbonyl- or halogen-substitutions, benzyl, benzanilide, $C_5$-$C_6$-cycloalky or naphthyl;

or where the $NR^4$ group combines with the A ring to form a 6-membered heterocycle optionally fused with a benzene ring, and $R^3$ is an unsubstituted phenylene or a phenylene substituted by one or more of alkyl-, alkoxy- or halogen-substitutions; and R is $C_1$-$C_4$-alkyl or phenyl.

2. A compound according to claim 1, wherein formula (II) is of the formula (IIa) or (IIb)

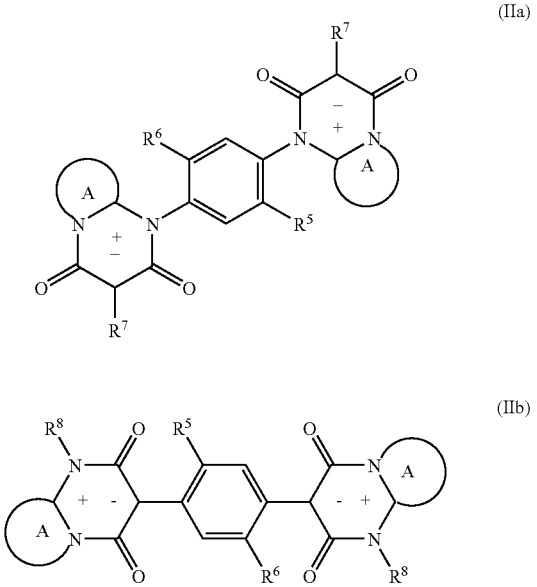

where
$R^5$ and $R^6$ are independently hydrogen, $C_1$-$C_4$-alkyl, $C_1$-$C_4$-alkoxy or halogen;

$R^7$ and $R^8$ are $C_1$-$C_4$-alkyl, $C_5$-$C_6$-cycloalkyl, a phenyl, benzyl, benzanilide or naphthyl that is unsubstituted or substituted by 1, 2, 3 or 4 radicals selected from the group consisting of $C_1$-$C_4$-alkyl, $C_1$-$C_4$-alkoxy, nitro, phenyl, $C_1$-$C_4$-alkoxycarbonyl, di($C_1$-$C_3$-alkyl)amino, di($C_1$-$C_3$-alkyl)aminocarbonyl, ($C_1$-$C_3$-alkyl)aminocarbonyl, aminocarbonyl and chlorine;

or where the $NR^8$ group combines with the A ring to form a 6-membered heterocycle optionally fused with a benzene ring.

3. A compound according to claim 2, wherein $R^5$ and $R^6$ are the same or different and are each hydrogen, methyl or chlorine.

4. A compound according to claim 1, wherein $R^3$, $R^4$, $R^7$ and $R^8$ is a substituted phenyl radical selected from the group consisting of 1-, 2-, 3-methyl-, ethyl-, methoxy-, ethoxy-, diethylamino-, chloro-, 2,5-dichloro-, 3-chloro-4-methyl-, 3-chloro-4-methoxy- and 4-nitrophenyl.

5. A compound according to claim 1, wherein formula (II) is of the formula (V)

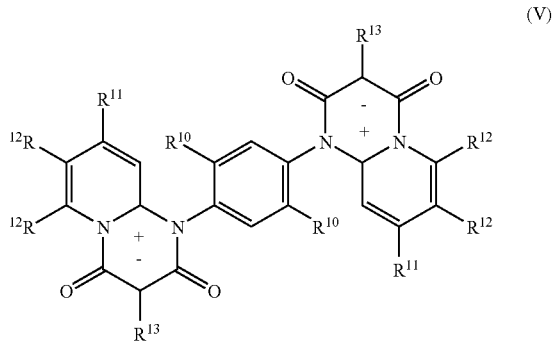

where
$R^{10}$ is hydrogen, methyl or chlorine,
$R^{11}$ is hydrogen or methyl,
$R^{12}$ is hydrogen, or two adjacent $R^{12}$ radicals together are a divalent $C_4H_4$ radical, and
$R^{13}$ is methyl or phenyl.

6. A compound according to claim 1 wherein formula (II) is of the formula (11) or (12)

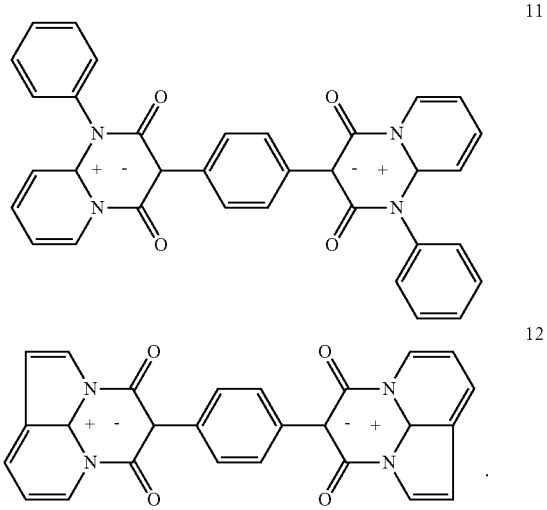

7. A process for preparing a compound according to claim 1, comprising the step of condensing either
(a) one equivalent of the compound of formula (III) where n is 2 with about two equivalents of the compound of formula (IV) where m is 1; or
(b) one equivalent of the compound of formula (IV) where m is 2 with about two equivalents of the compound of formula (III) where n is 1,

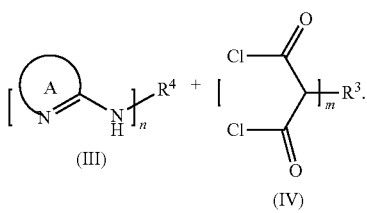

8. The process according to claim 7, wherein the condensing is effected in the presence of a base, wherein the base is triethylamine, pyridine, picoline, N-methylimidazole or alkali metal carbonate.

9. The process according to claim 7 wherein the compound of formula (II) is subjected to at least one of fine-dividing operation, wherein the fine-dividing operation is grinding, a a thermal treatment in an aqueous, aqueous-organic or organic medium at temperatures between 40° C. and 200° C., optionally under superatmospheric pressure.

10. A composition pigmented by a compound according to claim 1, wherein the composition is selected from the group consisting of plastics, resins, coatings, paints, electrophotographic toners, electrophotographic developers, electret materials, color filters, inks, inkjet inks, nonjettable printing inks, and seed.

* * * * *